United States Patent [19]

Farber

[11] 4,012,501
[45] Mar. 15, 1977

[54] HAIR-CARE COMPOSITION CONTAINING A THERMOPLASTIC POLYMER
[75] Inventor: Elliott Farber, St. Louis Park, Minn.
[73] Assignee: La Maur Inc., Minneapolis, Minn.
[22] Filed: May 8, 1975
[21] Appl. No.: 575,653
[52] U.S. Cl. .............................. 424/47; 8/127.51; 260/72.5 D; 260/77.5 R; 424/DIG. 1; 424/DIG. 2; 424/70; 424/71; 424/81; 526/263; 526/310; 526/330
[51] Int. Cl.$^2$ .......................................... A61K 7/11
[58] Field of Search .............. 424/DIG. 1, DIG. 2, 424/47, 71, 70; 260/80.72

[56] References Cited
UNITED STATES PATENTS

| | | | |
|---|---|---|---|
| 3,171,784 | 3/1965 | Witwer | 424/47 |
| 3,222,329 | 12/1965 | Grosser et al. | 260/80.5 |
| 3,405,084 | 10/1968 | Bohac et al. | 260/29.6 |
| 3,577,517 | 5/1971 | Kubot et al. | 424/47 |
| 3,743,715 | 7/1973 | Viout et al. | 424/47 |

*Primary Examiner*—Albert T. Meyers
*Assistant Examiner*—Vera C. Clarke
*Attorney, Agent, or Firm*—Whiteley and Caine

[57] ABSTRACT

The hair-care composition broadly comprises an ethanolic cosmetic vehicle and between about 1 and 20% by weight, based on the total weight of the composition, of film-forming thermoplastic resinous polymeric material which in dried condition is resistant to softening by humidity, insoluble in water alone but dispersible in water having a cosmetic pH, fully soluble in ethanol, and consists essentially of the addition free-radical polymerization product formed by polymerizing a monomeric mixture consisting essentially of, by weight percent: 1 to 20% of 1,1 dimethyl-1,(2-hydroxypropyl) amine methacrylimide; 8 to 45% of N-vinyl pyrrolidone; and 35 to 89% of vinyl acetate.

23 Claims, No Drawings

HAIR-CARE COMPOSITION CONTAINING A THERMOPLASTIC POLYMER

This invention relates to novel products for cosmetic uses, especially hair-care uses, and more particularly to products of improved composition containing a new thermoplastic polymeric material such as formed by polymerizing 1,1 dimethyl-1,(2-hydroxypropyl) amine methacrylimide, N-vinyl pyrrolidone, and vinyl acetate.

The most pertinent known prior art is set forth in the following United States Letters Patents, none of which teaches the new hair-care compositions hereof, nor the properties exhibited thereby, nor the new polymers in these new hair-care compositions: Grosser et al U.S. Pat. No. 3,222,329; Barabas et al U.S. Pat. No. 3,686,150; Viout et al U.S. Pat. No. 3,743,715; Barabas et al U.S. Pat. No. 3,803,104; and Basset et al U.S. Pat. No. 3,804,881.

The cosmetics industry, particularly in the field of hair-care preparations, has need of materials which, while having affinity to hair via physical and/or chemical bonds so as to have the effect of keeping a given coiffure set in its configuration, can ultimately be easily washed out of the hair. It is also desirable, once the hair is set, that the coiffure not be substantially affected by high humidities. Further, because acidic shampoos, conditioners, and creme rinses are used more and more frequently in today's cosmetic market, a need exists for hair-care preparations (such as hair sprays and hair setting lotions) wherein the non-volatile resinous polymeric material is soluble and/or dispersible in an acidic aqueous medium and also exhibits other properties satisfactory for cosmetic use.

There have been resinous materials used in the hair-care field, but these have been difficult to prepare either because of variation in the source of the natural raw materials or the technical difficulties of converting or neutralizing the materials (such as shellac) to achieve solubility or dispersibility in water. Furthermore, although most resinous materials used in hair-care products of today are soluble in an alkaline aqueous media, they unfortunately are compounded or made in such a way that they not only are insoluble in an acidic aqueous media but also tend to form sticky gummy precipitates in that media. This is undesirable when the use of acidic shampoos and creme rinses is prevalent.

The new hair-care preparations of this invention are formulated to contain thermoplastic polymeric material which exhibits strong affinity for human hair protein, which is not substantially affected by high humidity, which is at least dispersible (if not soluble) in aqueous media of cosmetic utility, including both alkaline and acidic aqueous media, and which can easily be removed, without the formation of sticky gummy precipitates, by shampooing it from the hair either in alkaline or acidic aqueous media.

A new hair-care composition according to this invention comprises an ethanolic cosmetic vehicle (present in a major amount of weight) and a small but significant amount by weight of the new film-forming resinous thermoplastic polymeric material distributed in that vehicle. Other ingredients may be and usually are present in hair-care compositions hereof, but the vehicle and polymeric constituent are critically present. Further, the polymeric material is of an especially critical nature. In dried condition, it is resistant to softening by humidity, is insoluble in water alone but is dispersible in water having a cosmetic pH, from an acid pH through an alkaline pH; and it is soluble in ethanol. It consists essentially of the addition free-radical polymerization product formed by polymerizing a monomeric mixture consisting essentially of, a weight percent: 1 to 20% of 1,1 dimethyl-1,(2-hydroxypropyl) amine methacrylimide; 8 to 45% of N-vinyl pyrrolidone; and 35 to 89% of vinyl acetate.

Other ingredients may be present in the aforenoted monomeric mixture, but not in such amount as to destroy the basic aforenoted properties for the resulting polymeric material nor the noted properties for the basic composition. Further, the ranges of selection for monomeric constituents to be polymerized is maintained so as to provide resulting copolymers having the properties critically specified above for the thermoplastic polymeric material of the composition. Also, while the conditions of polymerization may vary, desirably to gain polymeric material having additional improved properties even beyond those aforenoted, the illustrative conditions for polymerization discussed hereinbelow are much preferred.

A cosmetic vehicle is one which, as used in the hair-care applications hereof, is substantially non-toxic, non-irritating, and non-damaging of hair and skin. Ethanol is by far the most popularly acceptable constituent for the cosmetic vehicle; but water may optionally be present with it. Thus, the vehicle is characterized as "ethanolic", in that it includes ethanol as a critical constituent. It may consist essentially of ethanol (e.g., at least 80 or 90 weight percent or more) or contain other miscible vehicles (such as water) in admixture with the ethanol. The ethanol content will generally account for, at a minimum, at least about one-fifth of the weight of the total vehicle, or at least about one-sixth of the total weight of the composition. In hair sprays packaged or sealed or confined in aerosol containers, ethanol will account for essentially all or most of (at least 80 or 90% or more by weight) the vehicle constituent. In other words, the vehicle employed for hair spray compositions is capable of dissolving the polymeric material; and for this reason, the content of water (or other miscible liquid) is limited to that which does not destroy the capability of the ethanol concentration in the ethanolic vehicle to dissolve the polymeric material. (Volatile aerosol propellant material is not herein considered per se to be a constituent of the vehicle nor of the base hair-care compositions hereof.) In hair-setting lotions or cremes of the invention, water will customarily be employed in admixture with the ethanol, sometimes as much as about 80% water content for the vehicle being satisfactory. In the case of lotions or cremes, it is not critical that the polymeric material be dissolved in the vehicle, but the polymeric material of lotions or cremes is at least uniformly distributed in the vehicle by dispersion or emulsification. Further, a few percent of other ingredients, such as isopropyl alcohol, may optionally be included in the vehicle of the hair-care products hereof. It is commonly recognized that the ethyl alcohol known as "SD alcohol 40" contains a nominal few percent of ingredients for a denaturant function (i.e., tertiary butyl alcohol and brucine sulfate). A basic requirement for the vehicle of all compositions hereof is that it must be capable of effecting an essentially uniform distribution of the polymeric material in it.

Addition free-radical polymerization to form the film-forming thermoplastic resinous polymeric material can be accomplished under various conditions; solution, suspension, emulsion or bulk polymerization processes are useful. Because the polymer desirably is as repetitively regular in its chain as possible, the solution polymerization process is preferred over others. An alcoholic solvent media in which the monomers to be polymerized are soluble or miscible, and in which the resulting polymerization product is also soluble, is preferred; and ethanol is the preferred alcohol to employ.

Polymerization is most desirably accomplished under acid conditions, or with an acid added to the media of solvent polymerization, such that the pH of the media is between about 1.5 and 6.5, and generally around 5. A few illustrative useful acids to employ are adipic acid, acetic, benzoic, glutamic, boric, citric, oxalic, hydrochloric, fumaric, sulfuric, nitric, glycolic, succinic, and mixtures or combinations thereof. Adipic acid alone or acetic acid alone, or in combination with each other, or with other acids, is most preferred. The acid is used up or changed during polymerization, and becomes a part of the resulting polymer, not necessary as a link in the chain thereof, but as a radical attracted or united to sites (such as at the amine-imide nitrogens) on the 1,1 dimethyl-1,(2-hydroxypropyl) amine methacrylimide in the polymerization product. Thus, the acids can be said to cause the formation of an acid salt of that monomeric portion or unit; and the effect is the formation of an acid salt of that unit in the resulting polymer. Therefore, the polymerization product might be looked upon as that formed by addition free-radical polymerization of 1,1 dimethyl-1,(2-hydroxypropyl) amine methacrylimide, or equivalent—such as, an acid salt of it—with the N-vinyl pyrrolidone and the vinyl acetate of the monomeric mixture. Acids, when present, are considered herein to be a part of the reactable monomeric mixture, and may account for up to 20% of that mixture (but usually not over about 10% thereof).

A slight amount of cross-linking in the resulting polymer is also desirable, and increases the average molecular weight. A polyunsaturated monomer serving as a crosslinking agent is suitably added to the solvent media in which polymerization is accomplished. The very small amount used (usually less than one part by weight, based on 100 parts by weight of monomeric mixture) is dependent on its reactivity in the particular process conditions employed, and is that amount which effects sufficient cross-linking in the resulting polymerization product to increase its resistance to softening under high humidity conditions, as compared to the properties of a separate or second polymerization product identically formed except that the cross-linking agent is omitted. But the amount of cross-linking desired in the polymerization product is limited by solubility requirements. In general, the cross-linking must not be sufficient to cause the resulting product to form a gel in ethanolic cosmetic vehicles in which an otherwise identical polymer, formed without a cross-linking agent, is soluble. In a very real sense, the amount of cross-linking employed is insufficient to destroy solubility in ethanol. Suitable cross-linking agents are diallyl maleate, triallyl isocyanurate, triallyl cyanurate, allyl diglycol carbonate, diallyl fumarate, ethylene glycol dimethacrylate, and mixtures thereof. Of these, the most preferred is allyl diglycol carbonate. Although cross-linking agents frequently are used up as cross-linking is accomplished, and thus become a part of the resulting polymer, they are not considered to be part of this monomeric mixture in terms of calculating the weight percent thereof because of their specialized function and because of their almost negligible presence when calculated as phm (described hereinafter).

Polymerization is most preferably accomplished by incremental addition of at least the majority (over half, up to 90% or even more) of the N-vinyl pyrrolidone to the remaining parts of the monomeric mixture during the polymerization step. As noted above, the most desirable polymers are those which have regular or relatively uniform repetitive pattern of monomer distribution. Achieving this result is difficult and is enhanced when the monomer having the highest reactivity ratio, namely N-vinyl pyrrolidone, is incrementally added. The clarity and sparkle of polymer films is improved as the uniformity of the comonomer distribution in the resulting copolymers is improved. Clarity and sparkle for films of the polymer are desirable properties inasmuch as it is possible that a resin which produces a dull or hazy film could give hair a relatively dull or unappealing luster.

Further, for ease of preparation of polymeric material having the most useful and practical combination of properties for the compositions of the invention, the three primary constituents of the monomeric mixture are employed within the following more limited approximate ranges of weight percent: between 3% and 15% (or preferbly no more than 12%) of 1,1 dimethyl-1,(2-hydroxypropyl) amine methacrylimide; between 10% (or preferably at least 15%) and 35% of N-vinyl pyrrolidone; and between 45% (or preferably at least 50% or even 55%) and 82% of vinyl acetate.

Compositions hereof may also contain, and frequently will contain, such further or added optional ingredients as, for example, perfumes, plasticizers (e.g., diethyl phthalate, dioctyl phthalate, dialkyl adipates or sebacates, those perfumes or silicones having a plasticizing effect on the polymeric material, and others, alone or in combination), vitamins, panthenol, and allantoin, as well as still other ingredients which do not substantially alter the critical basic properties as aforediscussed. Plasticization of the polymeric material is frequently desirable to make it more flexible as it exists in film form on hair after the vehicle is evaporated. These optional ingredients account for no more than about one weight percent of the basic composition, and usually less. Stated another way, although the amount of these optional ingredients may account for as much as up to 10% by weight, based on the weight of the polymeric material alone, that amount is still minor and not a substantial part of the weight of the complete base composition of the invention.

A few illustrative non-limiting examples of the preparation of the thermoplastic polymeric material for the compositions hereof are set forth below. To be stressed is that the polymeric material or copolymers for the composition are formed by polymerizing a mixture approximately composed, in essential respects, of from 1 to 20% by weight of 1,1-dimethyl-1,(2-hydroxypropyl) amine methacrylimide (or its acid salt), 8 to 45% by weight of vinyl pyrrolidone, and 35 to 89% by weight of vinyl acetate. It is within this range of monomeric mixture that water insolubility (in water alone) of the resultant copolymer occurs, as required. But the resultant copolymer is dispersible in water of cosmetic pH, that is, a pH from about 3 or 4 to about 10 or 11 (which is about the extremes of pH considered cosmetically acceptable). The resultant polymer can also be dispersed in water of more extreme pH not of practical usage for cosmetic preparations.

Polymerization can be initiated by the usual sources of free-radical initiators such as peroxides, persulfates, peroxypivalates, percarbonates, azobisisobutyronitrile, azobisisovaleronitrile, and the like—by themselves or in combination with one another. The invention is not to be limited to any particular free-radical initiator system, or cross-linking agent, or reaction temperature. Initiator concentration, reaction temperature, as well as the use of polyunsaturated monomers for cross-linking can alter molecular weight; and this effect may be used similar to its use in other processes to change product properties related to molecular weight. Further, chain terminators such as carbon tetrachloride, dodecyl mercaptan and the like may be added to reduce the average molecular weight of the resin, if this is desired, provided the resultant polymer in dried condition is a solid (or non-liquid) having the necessary properties as aforediscussed.

In the following examples, the amount of each ingredient is specified in parts by weight (or weight percent) per 100 parts of monomers or polymerizable components of the monomeric mixture (i.e., per hundred monomer, phm). Thus, the total of the parts or percentages by weight for the ingredients making up the monomeric mixture equals 100; and the quantity of other ingredients (such as solvent, catalyst, and cross-linking agent) are specified in terms of the amount of percent which their weight bears to the 100 weight parts or weight percent for the monomeric mixture.

Solution polymerization was used in the following examples. "Solvent" refers to the alcoholic (ethanolic) solvent media. "Initiator" refers to Vazo 64 (azobisisobutyronitrile) of E. I. duPont de Nemours, Inc., Wilmington, Delaware. "Cross-linking agent" refers to allyl diglycol carbonate. "Amine-imide" is an abbreviation used to refer to 1,1 dimethyl-1,(2-hydroxypropyl) amine methacrylimide.

In all of the following examples of polymerization, the ingredients listed in tabular form were batch charged initially into an agitated reactor at room temperature. The contents were agitated until the solvent dissolved the other ingredients of the tabulation to form a uniform or homogeneous mixture. Further processing conditions are specified for each example.

Example 1

| Material | phm |
|---|---|
| Amine-imide | 10.00 |
| N-vinyl pyrrolidone | 2.50 |
| Adipic acid | 5.00 |
| Vinyl acetate | 75.00 |
| Initiator | 0.26 |
| Solvent | 61.00 |

The Beckman pH value of this system at room temperature was 4.0. The contents were continuously purged with nitrogen and heated to 68° C. After 2 hours at 68° C, incremental addition of 7.5 phm of N-vinyl pyrrolidone was started and accomplished at the rate of 1.25 phm per hour, with the addition completed after 6 hours. After a total reaction time of 18 hours, analysis of the solids content indicated a conversion of 96% of monomers to polymer.

Example 2

| Material | phm |
|---|---|
| Amine-imide | 10.00 |
| N-vinyl pyrrolidone | 4.10 |
| Adipic acid | 5.00 |
| Vinyl acetate | 70.00 |
| Initiator | 0.45 |
| Solvent | 63.00 |

The system was heated under a continuous nitrogen purge to a reaction temperature of 60° C. Then, after 2 hours at 60° C, incremental addition of 10.9 phm of N-vinyl pyrrolidone was initiated at a rate of 1.4 phm per hour, and completed after 8 hours. After 20 hours of reaction, 97% of the monomers were found to be converted to polymer.

Example 3

| Material | phm |
|---|---|
| Amine-imide | 5.00 |
| Adipic acid | 2.50 |
| N-vinyl pyrrolidone | 4.80 |
| Vinyl acetate | 65.00 |
| Initiator | 0.34 |
| Solvent | 60.50 |

The system was purged with nitrogen and heated to a reaction temperature of 68° C. After 3 hours at reaction temperature, incremental addition of 22.7 phm of N-vinyl pyrrolidone was started at a rate of 7 phm so that addition was complete in about 3 hours and 20 minutes. After a total reaction time of 12 hours, analyses indicated 99% conversion of monomers to polymer.

Example 4

| Material | phm |
|---|---|
| Amine-imide | 5.00 |
| N-vinyl pyrrolidone | 4.80 |
| Adipic acid | 2.50 |
| Vinyl acetate | 65.00 |
| Initiator | 0.23 |
| Solvent | 60.50 |

The above materials were purged with nitrogen, and brought to a reaction temperature of 68° C. Incremental addition of 22.7 phm of N-vinyl pyrrolidone was begun 1½ hours after the start of the reaction. Uniform incremental addition was completed within 3 hours and 20 minutes; i.e., at a rate of 7 phm/hour. The total reaction time at 68° C was 12 hours, giving 96% conversion of monomers to polymer.

Example 5

| Material | phm |
|---|---|
| Amine-imide | 5.00 |
| Adipic acid | 2.50 |
| N-vinyl pyrrolidone | 4.80 |
| Vinyl acetate | 65.00 |
| Cross-linking agent | 0.10 |
| Initiator | 0.23 |
| Solvent | 60.50 |

The system was purged with nitrogen and brought to its reaction temperature of 68° C. After 1½ hours at reaction temperature, 22.7 phm of N-vinyl pyrrolidone was added at the rate of 7.0 phm/hour. The total reaction time was 12 hours, giving 96% conversion of monomers to polymer.

Example 6

| Material | phm |
| --- | --- |
| Amine-imide | 5.00 |
| Adipic acid | 2.50 |
| N-vinyl pyrrolidone | 4.80 |
| Vinyl acetate | 65.00 |
| Cross-linking agent | 0.15 |
| Initiator | 0.20 |
| Solvent | 60.50 |

The system was purged with nitrogen to remove oxygen and heated to 68° C. One hour and 45 minutes after the reaction temperature was obtained, incremental addition of 22.7 phm of N-vinyl pyrrolidone was started at a rate of 5.7 phm/hour. The total reaction time was 12 hours, giving 96% conversion of monomers to polymer.

Example 7

| Material | phm |
| --- | --- |
| Amine-imide | 5.00 |
| N-vinyl pyrrolidone | 4.80 |
| Vinyl acetate | 67.50 |
| Cross-linking agent | 0.15 |
| Initiator | 0.20 |
| Solvent | 60.50 |

The system was purged with nitrogen and brought to 68° C. Then, after one hour and 45 minutes, incremental addition of 22.7 phm of vinyl pyrrolidone was initiated at a rate of 5.7 phm/hour. The total reaction time was 12 hours, at which time 96% conversion of monomer to polymer was noted.

Product Evaluation

The clarity and resistance to humidity of the polymerization products were determined on films cast from a 5% solids solution, using SD Alcohol 40 as the diluent. A 7 mil thick film was cast on a clean glass plate by the use of a "draw-down" blade supplied by the Gardner Instrument Company, Bethesda, Md.

The clarity of the dried films was rated as either hazy or clear. If there was any noticeable degree of haze to the film, it was rated as hazy. Table I lists the results.

Table 1

| Example | Clarity |
| --- | --- |
| 1 | Clear |
| 2 | Clear |
| 3 | Hazy |
| 4 | Clear |
| 5 | Clear |
| 6 | Clear |
| 7 | Clear |

The clarity of the films from Examples 1 and 2 illustrates that when 10 phm of 1,1 dimethyl-1,(2-hydroxypropyl) amine methacrylimide is used, a clear film is obtained under varying conditions of incremental addition of N-vinyl pyrrolidone and of initiator concentration. The haze of example 3 compared to the clarity of Example 4 illustrates the sensitivity of the degree of clarity and the copolymer uniformity on the initiator concentration and on the start and rate of the incremental addition of vinyl pyrrolidone. Examples 5 and 6 show that, when a small amount of a cross-linking agent is present, the film clarity is unaffected, provided the cross-linking agent is used at sufficiently low concentration so that no gel or insoluble copolymer fractions are formed. Furthermore, Examples 3 to 7 show how the start and rate of incremental addition of the fastest polymerizing monomer, i.e., N-vinyl pyrrolidone, is to be altered to gain clarity as initiator concentration is changed.

Cast films prepared as aforenoted were air dried for 2 hours and then placed in a humidity box kept at 78% relative humidity. After 10 minutes exposure in the humidity box, the Sward Hardness value (Sward Hardness Rocker, Model C, Gardner Labs., Bethesda, Md.) was determined. (The coiffure holding power—under high humidity and also, relatively speaking, in strong winds—of a hair spray resin is often correlated with its Sward Hardness.) Sward Hardness is measured by the number of times a precise calibrated metallic rocker can move on the surface of the film. As humidity affects the film, it becomes soft and the resistance offered to the rocker increases until movement of the rocker is slowed and ultimately stopped. The relatively high and desirable Sward Hardness values for the foregoing Examples are shown in Table II, together with the values for other known resins for comparative purposes.

Table II

| Example | Sward Hardness Value |
| --- | --- |
| 1 | 19 |
| 2 | 20 |
| 3 | 21 |
| 4 | 20 |
| 5 | 25 |
| 6 | 25 |
| 7 | 25 |
| Resin A (GAF-735 Copolymer) | 15 |
| Resin B (National Starch Resin 28-1310) | 17 |
| Resin C (GAF-335 Copolymer) | 19 |

Currently, shampoos and creme rinses are being produced with an acidic pH value; i.e., with a pH value from about 3.0 to 6.5. If a hair spray is used which contains a resin whose water solubility is dependent on an alkaline pH, then such resins may precipitate and/or gumout on a person's head if these acidic materials are used to wash out the water-soluble alkaline resin. Tests can be conducted by spraying a hair spray for 30 seconds from an aerosol can into a water system which is at a pH of 5.0 due to the addition of a small amount of acid and/or buffer.

Illustratively, a hair spray composition of this invention may consist of about 1.75 weight percent of the polymeric material of the invention dissolved in a cosmetic vehicle consisting essentially of ethanol (or consisting solely of SD alcohol 40) and accounting for the remaining weight percent of the base composition, except for any optional perfume or plasticizer as aforediscussed. For the tests set forth in Table III, no perfume or plasticizer was used. The base hair spray composition was mixed in equal parts by weight with a liquid volatile aerosol propellant (e.g., a mixture of trichlorofluoromethane and dichlorodifluoromethane). The mixture was sealed in an aerosol container having a dispenser valve, with the propellant under pressure at room temperature conditions.

The test results for aerosol spraying of resins from Examples above into acidic water for 30 seconds are shown in Table III; and the table also includes the results for other commercial hair spray resins under the same test conditions.

Table III

| Hair Spray | Effect |
|---|---|
| Containing 1.75% Resin from Example 1 | Clear |
| Containing 1.75% Resin from Example 2 | Clear |
| Containing 1.75% Resin from Example 3 | Clear |
| Containing 1.75% Resin from Example 4 | Clear |
| Containing 1.75% Resin from Example 5 | Clear |
| Containing 1.75% Resin from Example 6 | Clear |
| Containing 1.75% Resin from Example 7 | Clear |
| Composition A (National Starch/resin 28-1310) | Gummy Precipitate |
| Composition B (National Starch Amphomer) | Gummy Precipitate |
| Composition C (GAF-Gantrez 225) | Gummy Precipitate |

Further evaluation of 3 hair sprays prepared from resins of Examples 4, 5, and 6 above shows that sprays from Examples 5 and 6 have more body, crispness, and hold than a similar spray prepared from Example 4. Hence, it is seen that cross-linking improves some properties.

The 1,1 dimethyl-1,(2-hydroxypropyl) amine methacrylimide structure is shown below:

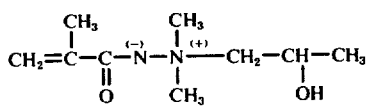

The polar charges of the amine-imide nitrogens produce an attractive force between resins containing this moiety and the polarizable keratin protein molecules of hair; and the teachings of this invention and the scope of the claims hereof are to be interpreted in the broad sense to include the use of equivalent monomers having this amine-imide force. The type of polar attraction noted is believed to be at least partially responsible for the ability of a coiffure finished with a spray containing a resin as shown in the Examples to maintain its hold under repeated combings even after using water in combing to slightly dampen the hair. Furthermore, such polar attraction is believed responsible for the high humidity resistance of these resins. It has also been observed that hair-sprays containing a resin as illustrated in Examples 1–7 have a much greater ability to prevent "fly-away" hair because the resin of the Examples helps to stop the development of static charges which cause repulsion between hair strands. That is, the polar charges on the amine-imide nitrogens act to neutralize and/or prevent the build-up of static electrical charges on the keratin molecules which it coats. Because of the polar forces between these hair spray resins and the protein molecules of hair, these copolymers of the Examples hereof have been observed to mend "split-ends", which is a useful characteristic of polymers in hair-care compositions.

Aerosol and/or non-aerosol hair sprays made with resins shown in the Examples produce a fine mist which on drying forces a thin continuous or discontinuous film of clear, glossy, and non-tacky character on the hair. Hair so coated exhibits excellent body, hold, and humidity resistance. Heads which are sprayed or set with a resin as illustrated in Examples 1–7 could be completely and easily washed by an acid-balanced shampoo or a shampoo or soap of alkaline nature.

For the most part, the base hair-spray compositions of the invention contain approximately 3.5% by weight of the polymeric material—or from about 1% by weight up to about 5% by weight of that ingredient dissolved in ethanol (with or without other ingredients such as aforediscussed). The base composition is mixed with up to (as a maximum) about two or three times, by weight, of aerosol propellant (i.e., a pressurized volatile liquid propellant) for aerosol packaging. Mixtures of about equal parts by weight of the base composition and aerosol propellant are especially useful for hair spray purposes.

Base hair-care compositions of the invention will normally contain a quantity of ethanolic vehicle sufficient to account for at least 60 or 70% or even at least 80% of the weight of the total composition. In the case of hair sprays, at least about 90% or even at least 95% of the weight of the total composition is preferably accounted for by the ethanolic vehicle. For lotions, the quantity of ethanolic vehicle (usually with water in the ethanol) preferably falls in the range of about 70 or 80% up to about 90 or 97% by weight of the total composition.

Setting lotions of the invention exhibit several noteworthy properties. The new polymeric material in them exhibits a desired degree of affinity for the hair such that upon combing, it does not flake-off the hair to produce the phenomena known as "dusting". Furthermore, the polymeric material imparts what might be called an elastic-like memory to the hair so that the original styled coiffure is substantially regained after comb-out. Illustratively, lotions may contain from about 3 to about 20% by weight (preferably at least about 5 up to about 15% by weight) of the polymeric material distributed (dissolved or dispersed) in an ethanolic vehicle. Minor amounts of other ingredients may also be present, as aforenoted. Also, dispersants or emulsifiers may be included, and preferably are, to facilitate dispersion of the polymeric material in the vehicle, especially when the vehicle includes the larger permissible quantities of water discussed above. Ethanolic vehicles for lotions may illustratively contain as little as 20% by weight ethanol and 80% water. The amount of water in the vehicle part of lotions will normally account for at least 10% of the weight of the ethanolic vehicle. An illustrative useful lotion may consist essentially of, by weight, 16% of the product of Example 6 (having approximately 60% polymeric material in solution), plus 2% propylene glycol, 0.25% perfume, 41% deionized water, and 40.75% ethanol (e.g., SD alcohol 40). Stated another way, this lotion contains, by weight percent, about 9.6% of the polymeric material of Example 6, plus about 2% propylene glycol, 0.25% perfume, 41% deionized water, and about 47.15 ethanol.

The small but significant amount of the polymeric material distributed in ethanolic cosmetic vehicles as taught herein will normally lie between about 1 and 20% by weight, based on the total weight of these new hair-care compositions. Indeed, the upper limit of polymeric material in the new compositions will most often not exceed about 15% (or even 10%) of the total weight of the compositions.

It is emphasized that all percentage figures given herein for the ingredients in the hair-care compositions hereof are based on the total composition completely apart from any aerosol propellant or the like. Thus, the terms "total composition" and "base composition", as used herein, refer to the ingredients of the total hair-care mixture or composition apart from any aerosol propellant. The propellant is not looked upon as being any part of the hair-care composition per se. When present, the propellant functions solely to propel the hair-care composition for spraying purposes.

While the invention is disclosed above with as much precision as possible in view of the nature of the subject matter, it is to be recognized that equivalents of specifically recited matter are likewise contemplated and intended, and that the claims are to be construed to comprehend the same.

That which is claimed is:

1. In a hair-care composition comprising an ethanolic cosmetic vehicle and between about 1 and 20% by weight, based on the total weight of said composition, of film-forming thermoplastic resinous polymeric material distributed in said vehicle, the improvement wherein said polymeric material in dried condition is resistant to softening by humidity, is insoluble in water alone but is dispersible in water having a cosmetic pH, from an acid pH through an alkaline pH, is soluble in ethanol, and consists essentially of the addition free-radical polymerization product of, by weight percent: 1 to 20% of 1,1 dimethyl-1,(2-hydroxypropyl) amine methacrylimide; 8 to 45% of N-vinyl pyrrolidone; and 35 to 89% of vinyl acetate.

2. The composition according to claim 1 wherein the portion of said polymerization product identified as 1,1 dimethyl-1,(2-hydroxypropyl) amine methacrylimide comprises an acid salt of said 1,1 dimethyl-1,(2-hydroxypropyl) amine methacrylimide.

3. The composition according to claim 2 wherein said acid salt comprises the adipic radical.

4. The composition according to claim 2 wherein said acid salt comprises the acetic radical.

5. The composition according to claim 1 wherein said polymerization product includes a cross-linking agent in an amount less than one part by weight based on 100 parts by weight for the components identified as 1,1 dimethyl-1,(2-hydroxypropyl) amine methacrylimide, N-vinyl pyrrolidone, and vinyl acetate, said polymerization product being cross-linked sufficiently to increase its resistance to softening by humidity, as compared to a second polymerization product otherwise identical except for said cross-linking, but is not cross-linked sufficiently to cause it to form a gel in ethanol.

6. The composition according to claim 5 wherein said cross-linking agent is selected from the group consisting of diallyl maleate, triallyl isocyanurate, triallyl cyanurate, allyl diglycol carbonate, diallyl fumarate, ethylene glycol dimethacrylate, and mixtures thereof.

7. The composition according to claim 5 wherein said cross-linking agent comprises allyl diglycol carbonate.

8. The composition according to claim 1 wherein said polymerization product forms a substantially clear dried film and is formed by solution polymerization with at least the majority of the weight of said N-vinyl pyrrolidone incrementally added during polyermization.

9. The composition according to claim 1, wherein said polymerization product additionally includes up to 20% by weight of an acid selected from the group consisting of acetic, benzoic, glutamic, adipic, boric, citric, oxalic, hydrochloric, fumaric, sulfuric, nitric, glycolic, succinic, and mixtures thereof, said acid being united at sites on said 1,1 dimethyl-1,(2-hydroxypropyl) amine methacrylimide.

10. The composition according to claim 9 wherein said acid comprises adipic acid.

11. The compositon according to claim 9 wherein said acid comprises acetic acid.

12. The composition according to claim 9 wherein said polymerization product forms a substantially clear dried film and is formed by solution polymerization with at least the majority of the weight of said N-vinyl pyrrolidone incrementally added during polymerization.

13. The composition according to claim 9 wherein said polymerization product includes a cross-linking agent in an amount less than about one part by weight based on 100 parts by weight for the components identified as 1,1 dimethyl-1,(2-hydroxypropyl) amine methacrylimide, N-vinyl pyrrolidone, and vinyl acetate, said polymerization product being cross-linked (i) sufficiently to increase its resistance to softening under humidity, as compared to a second polymerization product otherwise identical except for said cross-linking, and (ii) insufficiently to destroy the solubility of said polymerization product in ethanol.

14. The composition according to claim 1 wherein said 1,1 dimethyl-1,(2-hydroxypropyl) amine methacrylimide is present in said polymerization product in the form of an acid salt thereof, the acid forming said salt being selected from the group consisting of acetic, benzoic, glutamic, adipic, boric, citric, oxalic, hydrochloric, fumaric, sulfuric, nitric, glycolic, succinic, and mixtures thereof.

15. The composition according to claim 1, wherein the weight percent of components of said polymerization product lies in the following approximate ranges: between 3 and 15% of the 1,1 dimethyl-1,(2-hydroxypropyl) amine methacrylimide; between 10 and 35% of N-vinyl pyrrolidone; and between 45 and 82% of vinyl acetate.

16. The composition according to claim 1 wherein said vehicle comprises water in addition to ethanol.

17. The composition according to claim 1, wherein said composition additionally comprises a plasticizer for said thermoplastic polymeric material.

18. The composition according to claim 1, wherein said composition additionally comprises a perfume.

19. The composition according to claim 1, especially adapted for use as a hair-spray, and containing at least 95% by weight of said vehicle, and no more than about 5% by weight of said polymeric material in dissolved condition in said vehicle, and wherein said vehicle consists essentially of ethanol.

20. An aerosol container with a dispenser valve, within which a composition according to claim 19 is confined in admixed condition with a pressurized volatile liquid propellant, said propellant being present in a weight amount no greater than that approximately three times the total weight of said composition.

21. The composition according to claim 9, especially adapted for use as a hair spray, and containing at least 95% by weight of said vehicle, and no more than about 5% by weight of said polymeric material in dissolved condition in said vehicle, and wherein said vehicle consists essentially of ethanol.

22. The composition according to claim 1, especially adapted for use as a hair setting lotion, wherein said vehicle is at least 70% and not more than 97% of the weight of said composition, wherein between 10 and 80% of the weight of said vehicle is water and at least 20% of the weight of said vehicle is ethanol, and wherein said polymeric material is present in an amount of at least about 3% of the weight of said composition.

23. The hair setting lotion composition according to claim 22, wherein said polymeric material is at least about 5% up to about 15% of the weight of said composition.

* * * * *